United States Patent
Toone et al.

(10) Patent No.: US 7,935,847 B2
(45) Date of Patent: May 3, 2011

(54) NITROXYL ION SOURCE WITH SECOND ORDER REACTION NITROXYL RELEASE

(75) Inventors: Eric J. Toone, Durham, NC (US); David M. Gooden, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 12/532,939

(22) PCT Filed: Apr. 16, 2008

(86) PCT No.: PCT/US2008/004903
§ 371 (c)(1), (2), (4) Date: Dec. 29, 2009

(87) PCT Pub. No.: WO2008/130566
PCT Pub. Date: Oct. 30, 2008

(65) Prior Publication Data
US 2010/0094060 A1    Apr. 15, 2010

Related U.S. Application Data

(60) Provisional application No. 60/907,878, filed on Apr. 20, 2007.

(51) Int. Cl.
*C07C 207/00*   (2006.01)
*C07C 205/02*   (2006.01)
*C07C 205/04*   (2006.01)
*C07C 69/76*    (2006.01)
*C07C 69/95*    (2006.01)

(52) U.S. Cl. ........ 568/306; 568/924; 568/927; 568/949; 560/51

(58) Field of Classification Search ............... None
See application file for complete search history.

(56) References Cited

U.S. PATENT DOCUMENTS

| | | | |
|---|---|---|---|
| 6,359,182 B1 * | 3/2002 | Stamler et al. | 568/949 |
| 7,030,238 B2 | 4/2006 | Stamler et al. | |
| 7,049,308 B2 * | 5/2006 | Stamler et al. | 514/211.07 |

FOREIGN PATENT DOCUMENTS
WO    WO 02/34705 A2    5/2002

OTHER PUBLICATIONS

Database CAPLUS on STN, Acc. No. 2001:379135, Bakhvalov et al., Russian Journal of Organic Chemistry (translation of Zhurnal Organicheskoi Khimii) (2000), 36(11), p. 1601-1606 (abstract).*
David M. Gooden, Portion of Gooden thesis submitted for approval Apr. 19, 2006 titled "Synthesis and Physical Organic Chemistry of C-Nitroso Compounds: a study of C-Nitroso Ketones as Selective Nitrosonium Donors". *These were available to the public via catalog on Nov. 16, 2007.*
Gooden, D.M, et al, Current Topics in Medicinal Chemistry 2005, 5, 687-701.

* cited by examiner

*Primary Examiner* — Brian J Davis
(74) *Attorney, Agent, or Firm* — Bacon & Thomas, PLLC

(57) ABSTRACT

C-nitroso compound releases nitroxyl ion in blood in a second order reaction.

16 Claims, No Drawings

NITROXYL ION SOURCE WITH SECOND ORDER REACTION NITROXYL RELEASE

TECHNICAL FIELD

The invention is directed to a C-nitroso compound which is therapeutically active as a donor of nitroxyl ion.

BACKGROUND OF THE INVENTION

Nitric oxide (NO) donors are know to be useful for therapeutic utility, e.g., to prevent restenosis following angioplasty (Gloves, P., et al., Cardiovascular Research 26, 615-619 (1992)), to inhibit platelets to prevent coagulation and thrombus formation (Groves, P., et al., Circulation 87, 590-597 (1993)) and to treat angina (Knight, et al., Circulation 95, 125-132 (1997)). NO donors are considered to have additional therapeutic utility in treating cancer, killing microbes and viruses, relaxing airways and intestinal smooth muscle (e.g., for treating asthma and esophageal spasms), in promoting erectile function and in treatment of heart failure and urinary incontinence.

Nitric oxide can exist in three forms, namely in the oxidized form as nitrosonium ion ($NO^+$), as neutral nitric oxide (the stable free radical NO.) and in the reduced form as nitroxyl ion ($NO^-$).

The three forms are considered to have different physiological functions.

Administration of nitrosonium ion is favored for signaling receptors. The C-nitroso compounds that are the subject of the following set of patents where one of the inventors herein is a co-inventor, donate nitric oxide in the form of nitrosonium ion: see U.S. Pat. Nos. 6,359,182; 6,538,116; 6,887,994; 7,030,238 and 7,049,308. These C-nitroso compounds generate nitrosonium instead of nitroxyl because the nitroso is derived from a carbon acid with relatively low pKa so that there is no beta proton acidic enough to cause beta elimination between the nitroso and the beta proton.

Administration of neutral nitric oxide is favored for vasodilation and to inhibit aggregation of platelets.

Administration of nitroxyl ions increases cardiac output and reduces venous output for treatment of heart failure and protects against reperfusion injury.

A compound known to donate nitroxyl ion is Angeli's Salt, which is used to produce nitroxyl ion in situ. Angeli's salt decomposes in water to release nitroxyl and neutral nitric oxide. A problem with Angeli's salt is that it is associated with a single rate of delivery regardless of the rate of delivery required or most beneficial.

SUMMARY OF THE INVENTION

It has been concluded herein that deficiencies of Angeli's salt are because Angeli's salt provides nitroxyl ion by pseudo first order reaction so there is no control over the rate of delivery of nitroxyl ion, and it has been discovered that these deficiencies are overcome by nitroxyl ion donors that require second order reaction but not pseudo first order reaction, for nitroxyl ion production. This discovery allows control over the rate of nitroxyl ion delivery and makes possible treatment with nitroxyl ion of not only heart failure but also prophylactic use of nitroxyl for protection against reperfusion injury.

In one embodiment herein, the invention is directed to a C-nitroso compound which releases nitroxyl ion in human blood in a second order reaction. For example, this embodiment is directed to a C-nitroso compound having a molecular weight ranging from 75 to 1,000 grams/mol, which releases nitroxyl ion in a second order reaction in human blood, comprising a tertiary carbon atom, a nitroso group covalently bonded to the tertiary carbon atom, a carbon acid of pKa less than about 30 covalently bonded to the tertiary carbon atom, and an electron withdrawing moiety covalently bonded to the carbon acid, where the tertiary carbon is covalently bonded to or is a ring atom of a ring containing 5 or 6 carbon atoms, or the C-nitroso compound is acyclic and the carbon acid is a chain atom and at least one substituent on the tertiary carbon contains 4 to 20 carbon atoms. The compound undergoes reaction in the weakly alkaline milieu of human blood (pH of 7.4) or basic sites therein from example, thiol or amine in proteins including enzymes, to liberate by beta elimination between the carbon acid and the tertiary carbon, nitroxyl and a physiologically compatible corresponding alkene.

The electron withdrawing moiety acidifies the proton of the carbon acid. Varying the electron withdrawing moiety, allows varying the rate of generation of nitroxyl ion. Increasing the electron withdrawing strength of the electron withdrawing moiety increases the acidity of the carbon acid and thereby increases the rate of beta elimination. Thus varying electron withdrawing strength provides, for example, a bolus release (very high electron withdrawing strength) or a delayed or prolonged release (lesser electron withdrawing strength). The rate of nitroxyl release for practical use, can range from minutes to hours depending on the acidity of the carbon acid. The more acidic the carbon acid is, as provided by the electron withdrawing strength of the electron withdrawing group, the quicker the release. Thus, the invention herein allows control over the rate of nitroxyl ion release and variation from the rate of nitroxyl ion release from that of Angeli's salt.

As used herein, the teen "C-nitroso compound" means a compound in which a nitroso group is covalently bonded to a carbon atom. In this case, the nitroso group is covalently bonded to a tertiary carbon atom.

As used herein, the term "tertiary carbon atom" is used to mean a carbon atom singly bonded to three carbon atoms. The bonding of nitroso to a tertiary carbon is critical because otherwise there is essentially irreversible tantomerization to the corresponding oxime which is generally not active.

As used herein, the term "carbon acid" means compound that contains a CH group which dissociates to $C^-$ and $H^+$.

A carbon acid with a pKa less than about 30 is provided by the electron withdrawing group covalently bonded to the carbon acid.

As used herein, the term "first order reaction" means reaction where the reaction rate depends on reactant concentration raised to the first power.

As used herein, the term "second order reaction" means a reaction where the reaction rate depends on the concentration of one reactant raised to the second power or the concentrations of two different reactions each raised to the first power.

As used herein, the term "pseudo first order reaction" is a second order reaction where the concentration of one of the reactants is so large that it doesn't change appreciably during the course of the reaction so the reaction behaves as a first order reaction.

Angeli's salt reacts with a proton in water to release nitroxyl ion. Since the concentration of protons in water is large and doesn't change appreciably during the course of the reaction, Angeli's salt undergoes pseudo first order reaction in water.

Wikipedia shows the following reaction for the term "nitroxyl":

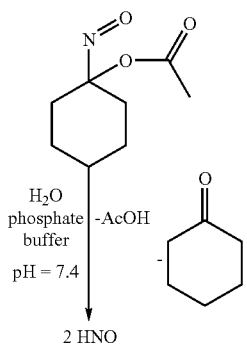

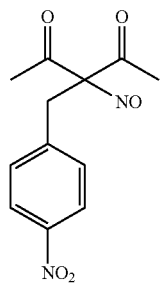
(I)

Since a reactant is water and the concentration of water doesn't change appreciably during the course of the reaction, the depicted reaction is a pseudo first order reaction.

Compounds of the invention herein are advantageous compared to those undergoing first order reaction or pseudo first order reaction, because varying the substituent on the carbon acid allows control over the rate of reaction and nitroxyl ion release.

DETAILED DESCRIPTION

In a first case, the compound has a substituent Q which is attached to the tertiary carbon and which consists of a chain moiety containing from 0 to 12 chain atoms consisting of 0 to 10 carbon atoms, 0 to 5 nitrogen atoms and 0 to 5 oxygen atoms covalently bonded to a cyclic moiety which is monocyclic, bicyclic, tricyclic, tetracyclic or pentacyclic and contains 5 to 24 ring atoms consisting of 2 to 20 carbon atoms, 0 to 4 nitrogen atoms, 0 to 2 oxygen atoms and 0 to 2 sulfur atoms. When the chain moiety consists of no chain atoms, the cyclic moiety is covalently bonded to the tertiary carbon.

In a second case, the tertiary carbon is a ring atom in a cyclic moiety which is monocyclic, bicyclic, tricyclic, tetracyclic or pentacyclic and contains from 5 to 24 ring atoms consisting of 2 to 20 carbon atoms, 0 to 4 nitrogen atoms, 0 to 2 oxygen atoms and 0 to 2 sulfur atoms where the ring atoms are counted by counting the atoms forming the ring(s), and exclude hydrogen and any other substituent on the ring. In this case, two of the carbon atoms attached to the tertiary carbon are part of the ring structure of the cyclic moiety.

In a third case, the C-nitroso compound is acyclic and at least one substituent on the tertiary carbon contains 4 to 20 carbon atoms.

Electron withdrawing groups are, for example, halo, including bromo, chloro, fluoro, iodo; p-nitrophenyl; p-halobenzyl, where halo is bromo, chloro, iodo or fluoro; p-acylbenzyl, including acetylbenzyl; acyl group, including, for example, acetyl and t-butyroyl; nitro group; —CN group; sulfonyl group; and carbonyl group. The following electron withdrawing groups are set forth with substituent with the highest electron withdrawing strength listed first followed by substituents in order of decreasing electron withdrawing strength: nitro, nitrophenyl, sulfonyl, cyano, fluoro, chloro, bromo, iodo, halobenzyl where the halo is fluoro, chloro, bromo or iodo, acyl including, for example, acetyl and t-butyroyl, p-acylbenzyl, including acetyl benzyl; and carbonyl.

It has been found herein that the rate of release is so fast, when the electron withdrawing group on the carbon acid is p-nitrophenyl, e.g., when the compound is (I) below.

that (I) cannot be isolated. The same would be true where the electron withdrawing group is nitro. Thus the compound of the invention excludes the cases where the electron withdrawing group is nitro or p-nitrophenyl.

Compounds within the scope of the invention of the first case are:

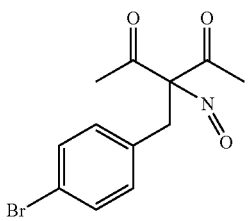
(II)

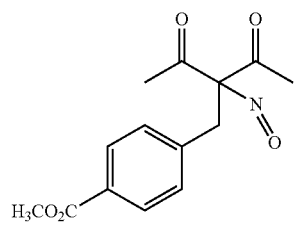
(III)

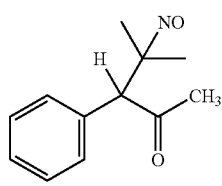
(IV)

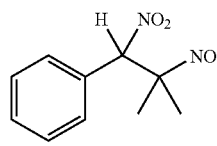
(V)

Examples of the compounds herein of the second case are:

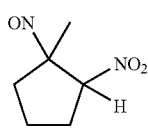
(VI)

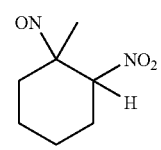

(VII)

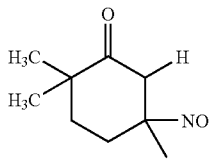

(VIII)

An example of the compound herein of the third case is:

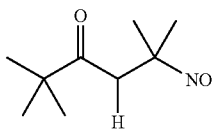

(IX)

Compounds (I), (II) and (III) are 3-benzyl-3-nitroso acetyl acetone derivatives.

We turn now to synthesis of the C-nitroso compounds herein.

Several methods applicable to synthesizing C-nitroso compounds are disclosed in Boyer, J. H., "Methods of Formation of the Nitroso Group and its Reactions" in The Chemistry of the Nitro and Nitroso Groups, Part 1, Feuer, H, Editor, John Wiley & Sons, New York (1969) at pages 215-299 and in Touster, O. in Organic Reactions, Vol. 7, John Wiley & Sons, New York (1955) at pages 327-377, and in Gowenlock, B. G., et al., Chem. Rev. 104 (7), 3315-3340 (July 2004), which are incorporated herein by reference.

Compounds (I), (II) and (III) are made in Working Examples below.

Compound (IV) can be prepared, for example, by addition of two equivalents of methyl Grignand to 1-cyano-1-phenyl-2-propanone in the presence of Ti(O-i-Pr)$_4$, followed by oxidation of the resulting primary amine to the corresponding c-nitroso compound.

Compound (V) can be prepared, for example, by aziridination of dimethyl styrene, opening of the aziridine with nitrogenous nucleophile, and selective protection/oxidation of the benzylic and tertiary nitrogens.

Compounds (VI) and (VII) can be prepared, for example, from methyl cyclopentene and methyl cyclohexene, respectively, by the sequence shown below.

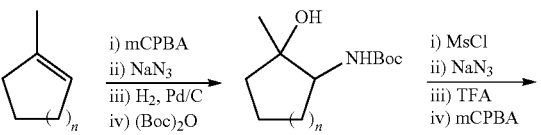

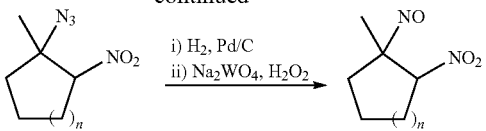

Compound (VIII) can be prepared, for example, from 3,5,5-trimethyl-2-cyclopentenone by conjugate addition of azide, reduction to the amine with hydrogen over Pd/C, and oxidation with sodium pertungstate in the presence of hydrogen peroxide.

Compound (IX) can be prepared, for example, by addition of 3,3-dimethyl-1-propyne to the methyl nitronium ester of acetone, followed by reductive cleavage of the aziridine and oxidation of the amine oxide to the nitroso compound.

The reaction to release nitroxyl is by beta elimination between the carbon acid and the tertiary carbon, that is by reaction of the nitroxyl and the proton of the carbon acid to generate HNO and the corresponding alkene, and is illustrated by the following reaction which occurs in weakly basic media, e.g., human blood and basic sites therein, for example, thiol and amine sites in proteins including enzymes.

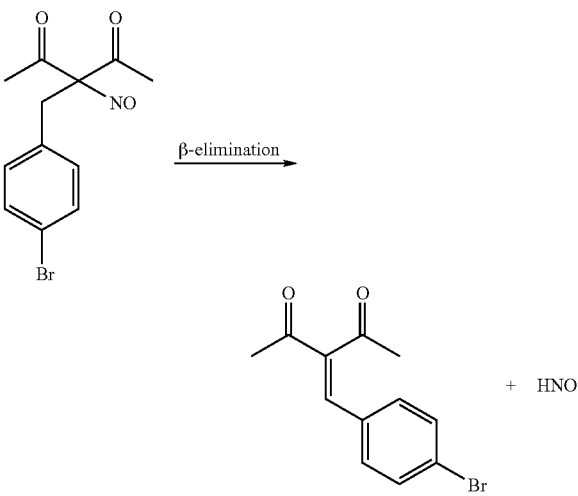

The HNO is the source of the nitroxyl radical since it decomposes in blood to form nitroxyl radical and water.

The alkene byproduct should be physiologically compatible, i.e., does not cause undue adverse physiological effects.

A key relation is between the basicity of what is abstracting the proton of the carbon acid and the pKa of the proton being abstracted.

We turn now to how to use.

The compounds of the first embodiment are administered for treatment or prophylaxis in cases where nitroxyl ion release produces beneficial result, e.g. for treatment of heart failure or to protect against reperfusion injury.

The compounds of the first embodiment are administered preferably in a concentration ranging from 1 nanomolar to 100 micromolar, for example, as an aqueous solution. The reason for the wide range is that many compounds are embraced by the invention.

Routes of administration include, for example, oral, parenteral including intravenous, inhaled, nebulized and topical.

The invention is illustrated by the following Working Examples.

Working Example I

Synthesis of Compound (II)

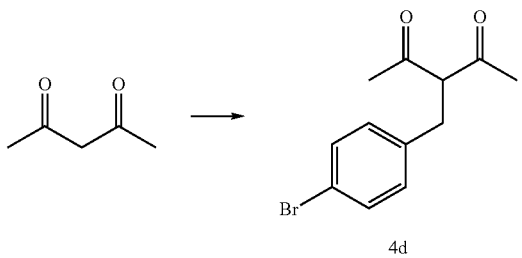

3-(4-bromobenzyl)-2,4-pentanedione (4d). Acetylacetone (4.5 mL, 44 mmol) was added dropwise over 30 minutes to a cooled (ice/H$_2$O bath) suspension of 95% NaH (0.95 g, 41 mmol) in anhydrous THF (150 mL). After H$_2$ evolution had ceased, a solution of p-bromobenzyl bromide (10.2 g, 40.8 mmol) in anhydrous THF (20 mL) was added at once with stirring. The reaction mixture was heated to 50° C. (internal temperature) for 48 h, cooled to room temperature, and poured into saturated aqueous NH$_4$Cl (250 mL). The organic phase was separated and the aqueous phase was extracted with EtOAc (3×125 mL). The combined organic extracts were dried (Na$_2$SO$_4$). The drying agent was removed by filtration and the filtrate was concentrated under reduced pressure to give an oily residue. Flash column chromatography (EtOAc:hexane (1:8)) gave 4d as a clear amber oil which solidified upon standing at room temperature (9.01 g, 82%). $^1$H NMR (300 MHz, CDCl$_3$): δ 7.42 (d, J=8.4 Hz, 2H, enol), 7.39 (d, J=8.4 Hz, 2H, keto), 7.03 (d, J=8.4 Hz, 2H, keto), 7.02 (d, J=8.4 Hz, 2H, enol), 3.95 (t, J=7.5 Hz, 1H, keto), 3.60 (s, 2H, enol), 3.10 (d, J=7.5 Hz, 2H, keto), 2.13 (s, 6H, keto), 2.05 (s, 6H, enol). $^{13}$C NMR (75 MHz, CDCl$_3$): δ 203.3, 192.1, 138.9, 137.3, 132.0, 130.6, 129.4, 120.0, 120.9, 108.1, 70.0, 33.7, 32.6, 29.9, 23.5. IR (neat, cm$^{-1}$): 3409, 3010, 3004, 2927, 1896, 1728, 1699, 1594, 1487, 1405, 1358, 1072, 1010. GC/MS (ET): m/z 268 (M$^+$). Anal. Calcd. for C$_{12}$H$_{13}$BrO$_2$: C, 53.55; H, 4.87; O, 11.89. Found: C, 53.27; H, 4.77; O, 11.61.

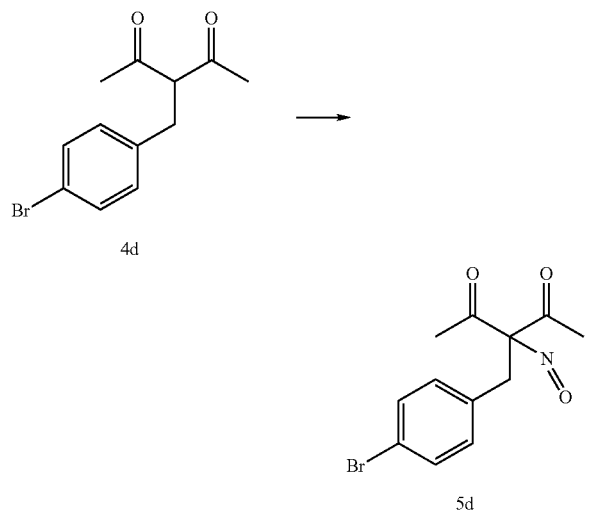

3-(4-bromobenzyl)-3-nitroso-2,4-pentanedione (5d). A freshly prepared solution of aqueous 10 M NaNO$_2$ (2.7 mL, 27 mmol) was added dropwise with stirring to a cooled (ice/H$_2$O bath) solution of 4d (6.00 g, 22.2 mmol) in glacial acetic acid (7 mL). Stirring was continued for 1 h. The reaction mixture was diluted with ice H$_2$O (10 mL) and precipitates were filtered off at the vacuum. The filter cake was washed with H$_2$O (100 mL), hexane (100 mL) and dried in vacuo to give the C-nitroso dimer as a pale white amorphous powder (3.52 g, 53%). $^1$H NMR (300 MHz, CDCl$_3$): δ 7.39 (d, J=8.7 Hz, 2H), 6.92 (d, J=8.7 Hz, 2H), 7.34 (d, J=8.7 Hz, 2H), 3.37 (s, 2H), 2.22 (s, 6H). $^{13}$C NMR (75.5 MHz, CDCl$_3$): δ 197.3, 132.7, 131.7, 130.4, 122.4, 92.2, 39.0, 29.0. IR (thin film, CHCl$_3$, cm$^{-1}$): 1710, 1718, 1490, 1415, 1358, 1290, 1220. MS (FAB): m/z 597 (MH$^+$), dimer. Anal. Calcd. for C$_{12}$H$_{12}$BrNO$_3$: C, 48.34; H, 4.06; O, 16.10. Found: C, 48.39; H, 4.09; O, 15.84.

Working Example II

Synthesis of Compound (III)

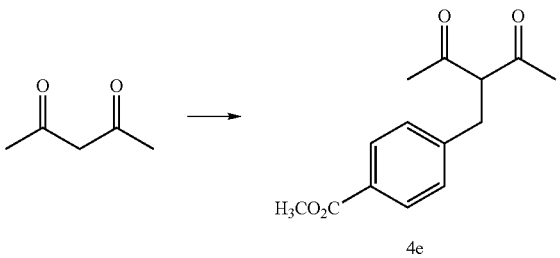

Methyl 4-(2-acetyl-3-oxo-butyl)-benzoate (4e). Acetylacetone (1.9 mL, 19 mmol) was added dropwise over 30 minutes to a cooled (ice/H$_2$O bath) suspension of 95% NaH (0.42 g, 18 mmol) in anhydrous THF (65 mL). After H$_2$ evolution had ceased, a solution of methyl (4-bromomethyl)benzoate (4.01 g, 17.5 mmol) in anhydrous THF (9 mL) was added at once with stirring. The reaction mixture was heated to 50° C. (internal temperature) for 48 h, cooled to room temperature, and poured into saturated aqueous NH$_4$Cl (125 mL). The organic phase was separated and the aqueous phase was extracted with EtOAc (3×100 mL). The combined organic extracts were dried (Na$_2$SO$_4$). The drying agent was removed by filtration and the filtrate was concentrated under reduced pressure to give an oily residue. Flash column chromatography (EtOAc:hexane (1:8)) gave 4e as a pale oil (3.78 g, 86%). $^1$H NMR (300 MHz, CDCl$_3$): δ 7.95 (d, J=8.1 Hz, 2H, enol), 7.92 (d, J=8.1 Hz, 2H, keto), 7.21 (d, J=8.1 Hz, 2H, keto), 7.20 (d, J=8.1 Hz, 2H, enol), 4.00 (t, J=7.5 Hz, 1H, keto), 3.88 (s, 3H, enol), 3.87 (s, 3H, keto), 3.67 (s, 2H, enol), 3.17 (d, J=7.5 Hz, 2H, keto), 2.11 (s, 6H, keto), 2.03 (s, 6H, enol). $^{13}$C NMR (75 MHz, CDCl$_3$): δ 203.2, 192.1, 167.1, 145.4, 143.7, 130.2, 128.9, 128.7, 127.7, 107.9, 69.7, 34.2, 33.3, 29.9, 23.5. IR (thin film, CHCl$_3$ cm$^{-1}$): 3420, 3002, 2953, 2844, 1935, 1732, 1710, 1609, 1346, 1359, 1272, 1178, 1109, 1019. MS (ESI): m/z 271 (M+Na). Anal. Calcd. for C$_{14}$H$_{16}$O$_4$: C, 67.73; H, 6.50; O, 25.78. Found: C, 67.69; H, 6.48; O, 25.81.

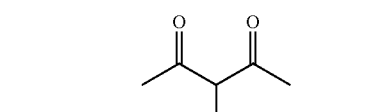

4e

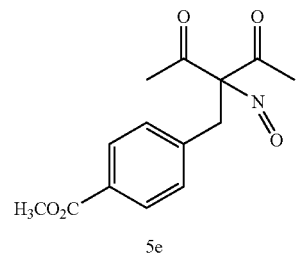

5e

Methyl 4-(2-acetyl-2-nitroso-3-oxo-butyl)-benzoate (5e). A freshly prepared solution of aqueous 10 M NaNO$_2$ (0.98 mL, 9.8 mmol) was added dropwise with stirring to a cooled (ice/H$_2$O bath) solution of 4e (2.02 g, 8.05 mmol) in glacial acetic acid (3 mL). Stirring was continued for 1 h. The reaction mixture was diluted with ice H$_2$O (5 mL) and precipitates were filtered off at the vacuum. The filter cake was washed with H$_2$O (50 mL), hexane (50 mL) and dried in vacuo to give the C-nitroso dimer as a white amorphous powder (0.957 g, 42%). $^1$H NMR (300 MHz, CDCl$_3$): δ 7.92 (d, J=8.1 Hz, 2H), 7.23 (d, J=8.1 Hz, 2H), 3.88 (s, 3H), 3.40 (s, 2H), 2.22 (s, 6H). $^{13}$C NMR (75 MHz, CDCl$_3$): δ 197.7, 167.0, 144.5, 129.6, 127.9, 127.7, 92.4, 67.8, 39.3, 29.1. IR (thin film, CHCl$_3$, cm$^{-1}$): 3016, 2958, 1725, 1715, 1609, 1433, 1358, 1285, 1195, 1178, 1110. MS (FAB): m/z 555 (MH$^+$), dimer. Anal. Calcd. for C$_{14}$H$_{15}$NO$_5$: C, 60.64; H, 5.45; N, 5.05; O, 28.85. Found: C, 60.59; H, 5.59; O, 28.89.

Working Example III

Synthesis of Compound (I)

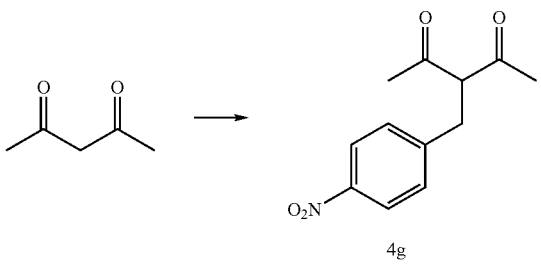

4g 3-(4-nitrobenzyl)-2,4-pentanedione (4g). A mixture of nickel(II)acetylacetone dihydrate (3.54 g, 12.1 mmol) and 4-nitrobenzylchloride (2.09 g, 12.2 mmol) in anhydrous DMSO (18 mL) was heated at 100° C. (internal temperature) for 22 h. The reaction mixture was cooled to room temperature, poured into H$_2$O (100 mL) and extracted with Et$_2$O (6×50 mL). The combined organic phases were washed with water (3×100 mL) and dried (Na$_2$SO$_4$). The drying agent was removed by filtration and the filtrate was concentrated under reduced pressure. Purification of the oily residue by flash column chromatography (EtOAc:hexanes (1:8)) gave 4g as a yellow solid (1.43 g, 51%). $^1$H NMR (300 MHz, CDCl$_3$): δ 8.18 (d, J=8.7 Hz, 2H, keto), 8.14 (d, J=8.7 Hz, 2H, enol), 7.34 (d, J=8.7 Hz, 2H, keto), 7.32 (d, J=8.7 Hz, 2H, enol), 4.01 (t, J=7.5 Hz, 1H, keto), 3.77 (s, 2H, enol), 3.25 (d, J=7.5 Hz, keto), 2.16 (s, 6H, keto), 2.06 (s, 6H, enol). $^{13}$C NMR (75.5 MHz, CDCl$_3$): δ 202.4, 192.1, 147.7, 146.0, 129.9, 128.4, 124.2, 124.1, 107.3, 69.7, 35.9, 33.9, 33.4, 30.1, 23.7. IR (thin film, CHCl$_3$, cm$^{-1}$): 3106, 3077, 3049, 2934, 1602, 1593, 1516, 1417, 1355. GC/MS (EI): m/z 235 (M$^+$).

A freshly prepared solution of aqueous 10M NaNO$_2$ (0.59 ml, 5.9 mmol) is added dropwise with stirring to a cooled (ice/H$_2$O bath) solution of (1.22 g, 4.9 mmol) 4g in glacial acetic acid (1.5 ml). Stirring is continued for 1 hour. The reaction mixture is diluted with the water (5 mL) and precipitates are filtered off at vacuum. The filter cake is washed with water (20 ml), hexane (20 ml) and dried under vacuum to give

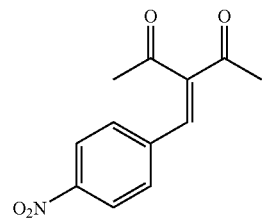

5

The obtaining of 5 shows that (I) was obtained but couldn't be isolated and that nitroxyl was released before isolation of compound (I) could be had.

Working Example IV

Treatment of Heart Failure

A 60 year old with congestive heart failure and a dilated cardiomyopathy is administered compound (II) intravenously (to obtain a blood concentration of 10 nanomolar). His ejection fraction improves, his blood pressure decreases, and his pO2 improves on room air. Symptoms of angina also decrease.

Working Example V

Prevention of Ischemic Reperfusion Injury

A 45 year old male presents with a heart attack. Blockage is treated with bypass surgery. The patient is give compound (II) intravenously to maintain a blood concentration of 10 nanomolar 15 minutes before reperfusion up to 20 minutes thereafter. Ischemic reperfusion injury does not occur.

Variations

The foregoing description of the invention has been presented describing certain operable and preferred embodiments. It is not intended that the invention should be so limited since variations and modifications thereof will be obvious to the skilled in the art, all of which are within the spirit and scope of the invention.

What is claimed is:

1. A C-nitroso compound having a molecular weight ranging from 75 to 1000 grams per mole which releases nitroxyl ion in human blood in a second order reaction but not in a pseudo first order reaction, comprising a tertiary carbon atom, a nitroso group covalently bonded to the tertiary carbon atom, a carbon acid of pKa less than about 30 covalently bonded to the tertiary carbon atom, and an electron withdrawing moiety covalently bonded to the carbon acid, where the tertiary carbon is covalently bonded to a ring atom of a ring containing 5 or 6 carbon atoms, the C-nitroso compound having a substituent Q which is attached to the tertiary carbon and which consists of a chain moiety containing from 0 to 12 chain atoms consisting of 0 to 10 carbon atoms, 0 to 5 nitrogen atoms and 0 to 5 oxygen atoms covalently bonded to a cyclic moiety which is monocyclic, bicyclic, tricyclic, tetracyclic or pentacyclic and contains 5 to 24 ring atoms consisting of 2 to 20 carbon atoms, 0 to 4 nitrogen atoms, 0 to 2 oxygen atoms and 0 to 2 sulfur atoms and when the chain moiety consists of no chain atoms, the cyclic moiety is covalently bonded to the tertiary carbon;

the electron withdrawing moiety being selected from the group consisting of sulfonyl, cyano, fluoro, chloro, iodo, bromo; halobenzyl where the halo is fluoro, chloro, bromo, iodo; acyl selected from the group consisting of acetyl and t-butyroyl; acetylbenzyl; and carbonyl.

2. The C-nitroso compound of claim 1 which comprises a 3-benzyl-3-nitroso acetyl acetone moiety.

3. A C-nitroso compound having a molecular weight ranging from 75 to 1000 grams per mole which releases nitroxyl ion in human blood in a second order reaction but not in a pseudo first order reaction comprising a tertiary carbon atom, a nitroso group covalently bonded to the tertiary carbon atom, a carbon acid of pKa less than about 30 covalently bonded to the tertiary carbon atom, and an electron withdrawing moiety covalently bonded to the carbon acid, where the tertiary carbon is a ring atom in a cyclic moiety which is monocyclic, bicyclic, tricyclic, tetracyclic or pentacyclic and contains from 5 to 24 atoms consisting of 2 to 20 carbon atoms, 0 to 4 nitrogen atoms, 0 to 2 oxygen atoms and 0 to 2 sulfur atoms where the ring atoms are counted by counting the atoms forming the ring(s), and exclude hydrogen and any other substituent on the ring and the electron withdrawing moiety is

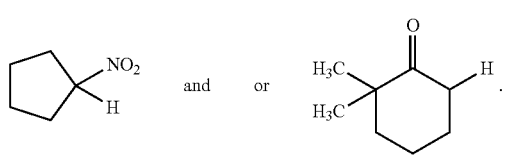

4. A C-nitroso compound having a molecular weight ranging from 75 to 1000 grams per mole which releases nitroxyl ion in human blood in a second order reaction but not in a pseudo first order reaction, comprising a tertiary carbon atom, a nitroso group coalvently bonded to the tertiary carbon atom, a carbon acid of pKa less than about 30 covalently bonded to the tertiary carbon atom, and an electron withdrawing moiety covalently bonded to the carbon acid wherein the C-nitroso compound is acyclic and the carbon acid is a chain atom and at least one substituent on the tertiary carbon contains 4 to 20 carbon atoms; where the electron withdrawing moiety comprises

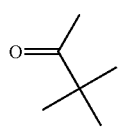

5. The C-nitroso compound of claim 1 where the electron withdrawing moiety is bromobenzyl.

6. The C-nitroso compound of claim 5 which is

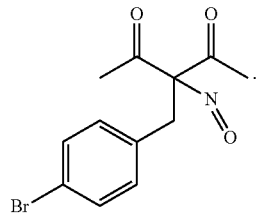

(II)

7. The C-nitroso compound of claim 2 which is

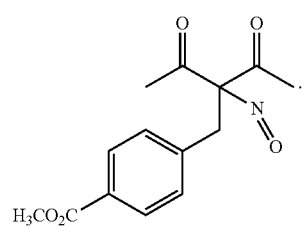

(III)

8. The C-nitroso compound of claim 1 where the electron withdrawing moiety is acetyl.

9. The C-nitroso compound of claim 8 which is

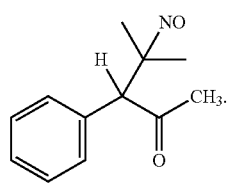

(IV)

10. The C-nitroso compound of claim 3 which is

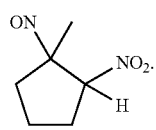

(VI)

11. The C-nitroso compound of claim 3 which is

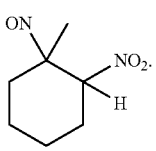

(VII)

12. The C-nitroso compound of claim 3 which is
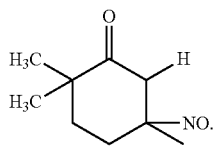 (VIII)
13. The C-nitroso compound of claim 4 which is
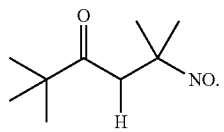 (IX)
14. A c-nitroso compound which is
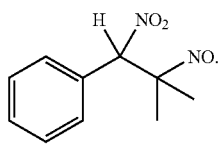 (V)
15. The C-nitroso compound of claim 1 where the pKa of the carbon acid is greater than the pKa of the carbon acid of
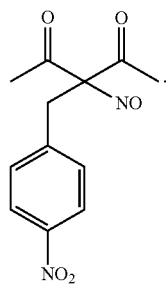 (I)
16. The C-nitroso compound of claim 1 where the pKa of the carbon acid is at least as great of the carbon acid of
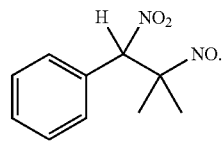 (V)
* * * * *